United States Patent [19]
Aiyer et al.

[11] Patent Number: 5,777,729
[45] Date of Patent: Jul. 7, 1998

[54] WAFER INSPECTION METHOD AND APPARATUS USING DIFFRACTED LIGHT

[75] Inventors: Arun A. Aiyer, Fremont; John H. McCoy, San Carlos, both of Calif.; Kyoichi Suwa, Tokyo, Japan; Henry K. Chau, San Francisco, Calif.

[73] Assignee: Nikon Corporation, Japan

[21] Appl. No.: 644,649

[22] Filed: May 7, 1996

[51] Int. Cl.$^6$ .................................................. G01N 21/00
[52] U.S. Cl. ........................ 356/237; 336/394; 336/448; 336/318
[58] Field of Search ..................... 356/237, 394, 356/448, 318

[56] References Cited

U.S. PATENT DOCUMENTS

| | | | |
|---|---|---|---|
| 4,660,980 | 4/1987 | Takabayashi et al. | 356/357 |
| 4,707,611 | 11/1987 | Southwell | 250/560 |
| 4,899,055 | 2/1990 | Adams | 250/372 |
| 5,034,617 | 7/1991 | Isobe | 250/560 |
| 5,164,603 | 11/1992 | Hartman et al. | 250/572 |
| 5,576,833 | 11/1996 | Miyoshi et al. | 356/237 |
| 5,640,237 | 6/1997 | Esrig et al. | 356/237 |

FOREIGN PATENT DOCUMENTS

| | | |
|---|---|---|
| 5-45862 | 2/1993 | Japan. |
| 5-232032 A | 9/1993 | Japan. |
| 8-075661 A | 3/1996 | Japan. |

Primary Examiner—Frank G. Font
Assistant Examiner—Reginald A. Ratiff
Attorney, Agent, or Firm—Skjerven, Morrill, MacPherson, Franklin & Friel LLP; Norman R. Klivans

[57] ABSTRACT

Defects in a processed or partly processed semiconductor wafer, or other similar three-dimensional periodic pattern formed on a substrate surface, are detected by light diffraction. Incident monochromatic light is provided from an elongated and extended source to illuminate the entire wafer surface. By use of automated image processing techniques, wafer macro inspection is thereby automated. The elongated and extended light source allows light at different angles to be incident upon each point of the wafer surface, thereby allowing defect detection for an entire wafer surface in a single field of view and reducing inspection time. The particular wavelength of the incident monochromatic light is predetermined to allow optimum detection of defects in the periodic pattern on the wafer, depending on the width and pitch of the features of the periodic pattern.

40 Claims, 13 Drawing Sheets

WAFER INSPECTION METHOD AND APPARATUS USING DIFFRACTED LIGHT

BACKGROUND OF THE INVENTION

1. Field of the Invention

This invention relates to finding defects in a planar substrate having a periodic structure defined on its surface, and more specifically to inspecting fabricated semiconductor wafers for defect sites.

2. Description of the Prior Art

A well-known problem in the semiconductor industry is the need to inspect for defects the wafers on which e.g. integrated circuits are formed. This inspection may take place numerous times during the semiconductor fabrication process, for instance once for each fabricated layer. Prior art inspection techniques involve a human being holding the wafer and illuminating it with a light and examining it visually for defects. Typical defects result from a failure to replicate the desired pattern in the metallization, polysilicon structures, photoresist, trenches, etc. Such defects result in a portion of the completed integrated circuit or device not functioning properly and hence it is important that the wafers be periodically inspected during fabrication. It is also important to pinpoint the location of each defect site so that portion of the wafer can be indicated as not usable.

The prior art relies on manual inspection of wafers under polychromatic light. Light diffracted by the wafer can reveal defect sites. However, the presence of many wavelengths can reduce detection sensitivity. Moreover, manual inspections can be unreliable and time consuming. Hence while it is known to use light scattered from the surface of the wafer to locate defects, this process has the disadvantage of being time consuming because each portion of the wafer must be placed under the light source and inspected, with only a small area of the wafer being inspected at any one instant.

SUMMARY

In accordance with the present invention, defects in a periodic structure (a three dimensional structure) formed on the surface of a substrate such as a semiconductor wafer are detected using a diffraction technique. The present method and apparatus uses an extended (and elongated) source of the incident light. ("Light" here is not restricted to the visible spectrum, but refers to electro-magnetic energy that can be diffracted.) This allows the entire wafer surface, e.g. for a wafer 12 inches in diameter, to be inspected in a single field of view. By using image processing techniques, wafer macro inspection is thereby automated. Thus advantageously in accordance with the invention, macro inspection of each wafer, for each and every process step, is enabled. Also by use of automated image processing, the uncertainties of manual (human) inspection are avoided while the elongated source makes possible inspection of an entire wafer in a single field of view, hence reducing wafer handling and increasing throughput.

Thus in accordance with the invention the so-called "Class 2" defect types in fabricated semiconductor wafer structures caused by problems such as focus offset, defocus due to a particle under the wafer, errors in wafer development, etching, stripping procedures, and insufficient developer are detected.

In accordance with the invention not only semiconductor wafers can be inspected, but also other very small periodic structures such as diffraction gratings or micro-machined structures. All these structures are referred to herein generically as "gratings".

That is to say, a "good" portion of the grating surface (having no defects) has a certain diffraction efficiency which differs from that of defect sites. By use of the elongated and extended light source, every point on the grating receives light from appropriate points on the elongated light source. Thus the entire grating may be inspected in one field of view. The length and width of the light source is a function of the size of the grating (work piece) being inspected as well as the range of grating pitch e.g. on the wafer.

In accordance with the invention, a monochromatic light is used for grating inspection, with the wavelength of the light determined by the geometry of the grating periodic structure features, i.e. their width and pitch (distance between adjacent features). The detection apparatus can take various forms. In one embodiment a single detector (for instance a charge coupled device video camera) is positioned at a single predetermined angle to detect the light reflectively diffracted from the grating, the light being incident from the elongated source. In another embodiment where a particular grating includes features of several different pitches (patterns), the detector is moved to several predetermined angles to inspect each of the different patterns. In another embodiment, several different detectors are located at different angles of reflective diffraction to receive light diffracted from the various patterns. In yet another embodiment, instead of using multiple detectors at different angles, a turning mirror is tilted through the various angles thereby reflecting the diffracted light to a single fixed detector camera.

It is to be understood that typically in the semiconductor field, a single wafer may have features of different pitches. For instance a memory portion of a semiconductor die is typically a uniform pattern having a fixed pitch. On the other hand, another semiconductor wafer having a different type of memory pattern is likely to have a different pitch. Other types of wafers such as those having microprocessor die will have a variety of pitches on each die, depending on whether a particular portion of the die is memory or logic. In this case each portion of the die is inspected separately using a different incident light wavelength in order to detect defect sites.

It has been found that in accordance with the present invention that monochromatic light improves contrast for finding defect sites in the grating (compared to polychromatic light), due to less contrast being available with the polychromatic light.

It is of course not necessary in accordance with the invention to inspect an entire grating at once; it is also possible to merely inspect a portion of the grating, e.g. one half or one third, at one time. This is especially advantageous for a very large grating when one wants to limit the size of an inspection station which incorporates the present invention. Also in accordance with the present invention, the grating inspection is undertaken at two orientations of the wafer in its XY plane, e.g. the grating is first inspected at a particular orientation and then is inspected again after being rotated through 90°. This is done for instance by mounting the grating on a turntable. The advantage of this is that it helps to pick the orientation that provides the maximum S/N (signal/noise) ratio for defect detection.

Also in accordance with the present invention, one light source provides multiple wavelengths of the incident light, each wavelength being adapted for a particular feature pitch size. Hence one can inspect for several different feature pitches during wafer inspection.

In one embodiment of the invention, the grating images as received by the detector(s) are processed using commercially available "machine vision" circuitry and the processed images analyzed by commercially available software. Other image processing techniques may be substituted.

In accordance with one embodiment of the present invention, inspection is carried out by a stand alone inspection machine but this apparatus may be incorporated into other suitable (semiconductor) processing equipment if so desired.

DETAILED DESCRIPTION

Figure 1:
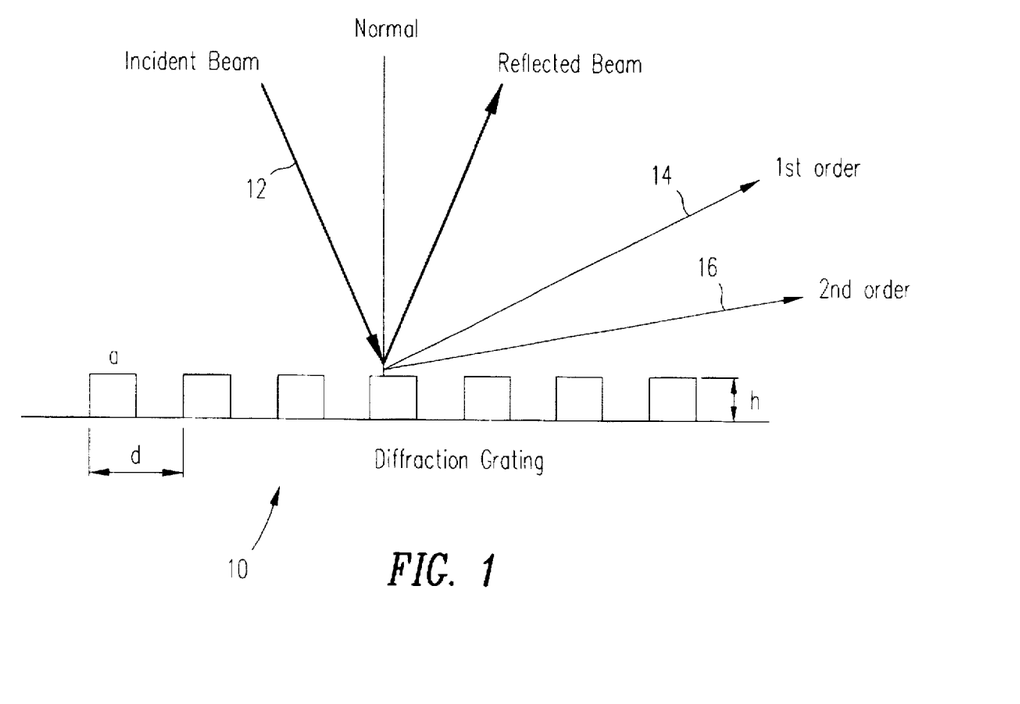
FIG. 1 illustrates diagrammatically diffraction from a periodic structure, e.g. a surface of a processed semiconductor wafer.

Consider a reflection grating 10 (e.g. a periodic structure (pattern) such as on a semiconductor wafer) with feature width a and grating pitch d as shown in FIG. 1 in a side view. A change in the a/d ratio affects the intensity of diffracted light $I_m$. If that occurs within an exposure field then $I_m$ varies within that field. An alteration in feature width a may occur due to focus offset, field curvature, defocus due to particles under the wafer or due to variations in the process conditions in a photolithographic process used to form grating 10. By observing intensity variation within different diffraction orders (e.g., first order 14 and second order 16 as shown in FIG. 1), the presence of defects in the pattern due to the above mentioned causes is detected.

When light 12 of wavelength λ is incident at angle $\theta_i$, the direction of diffraction $\theta_m$ of the mth order is determined from:

$$d(\sin\theta_m - \sin\theta_i) = \pm m\lambda$$

Figure 2:
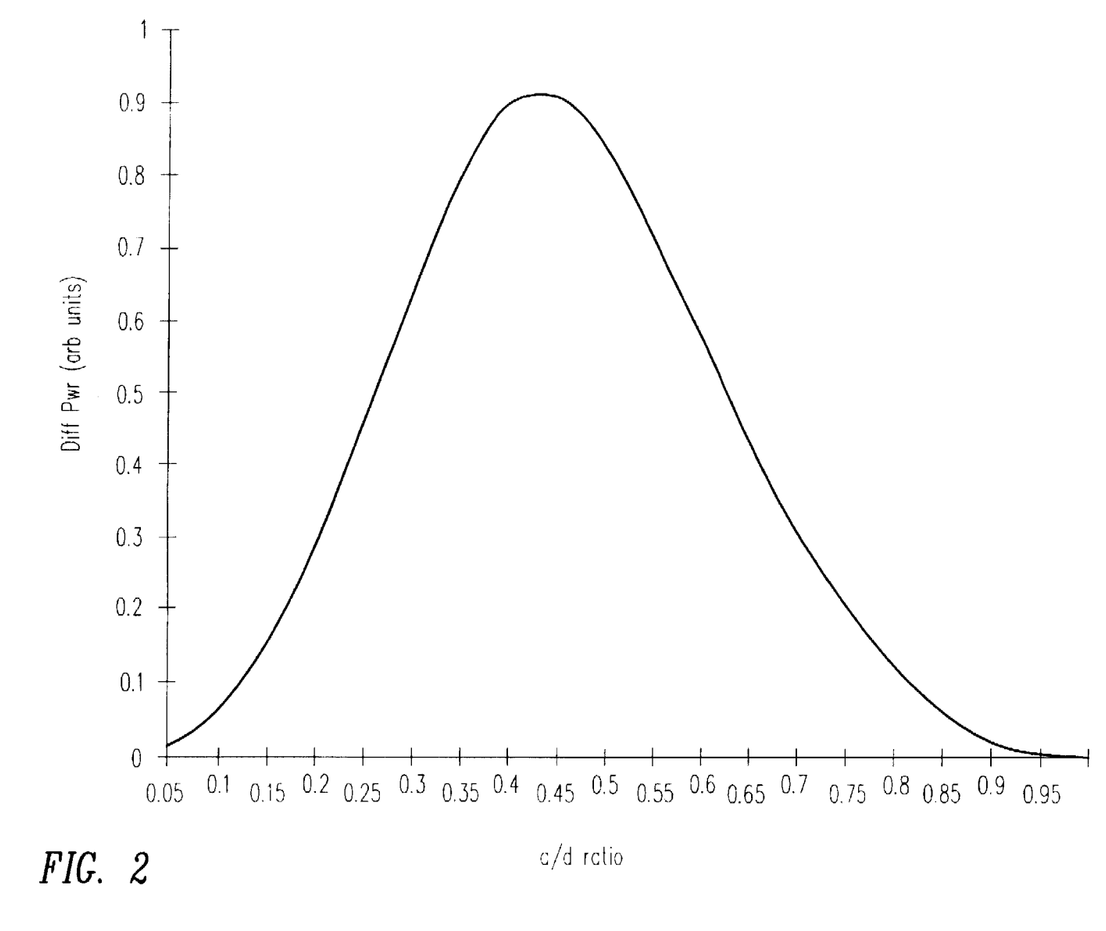
FIG. 2 depicts the diffraction power (diffracted light intensity) as a function of feature width to feature pitch.

The intensity of mth order light from a grating with a 90° wall angle as shown in FIG. 1 is given by:

$$I_m \propto I_0 N^{2} * [\sin^{2}(\pi m a/d)]/(\pi m)^{2}$$

where N is the number of line/space pairs of the features on the grating surface. A plot of the change in $I_m$ due to variation in a/d ratio is shown in FIG. 2 for diffraction orders m=1. In semiconductor processing, "Class 2" defect types such as focus offset, defocus due to a particle under the wafer, error in wafer development etching and stripping procedures, and defects caused by insufficient developer cause a localized change in the a/d ratio and/or change in aperture function and hence can be detected via corresponding localized changes in diffraction efficiency.

Figure 3A:
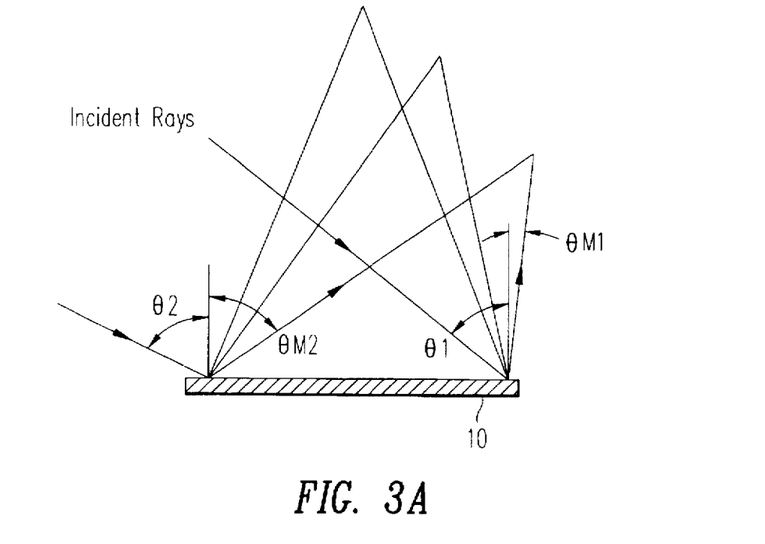
FIG. 3A depicts incident and diffracted light and the relevant angles for two incidence angles.
Figure 3B:
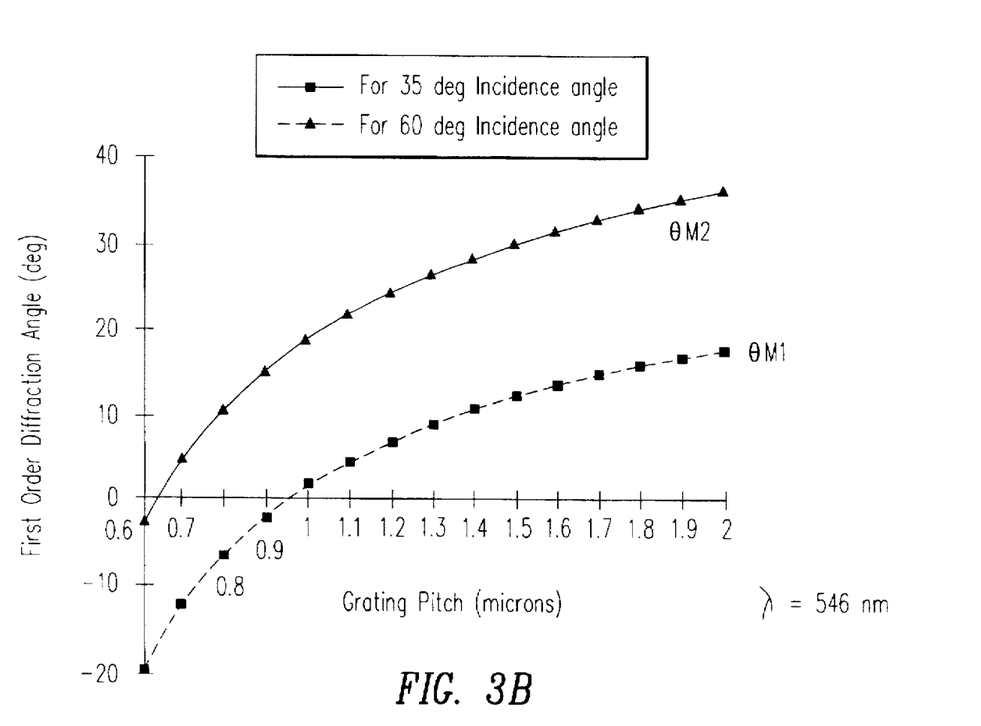
FIG. 3B is a plot showing the variation in diffraction angle as a function of grating pitch for two incidence angles, as in FIG. 3A.

In accordance with one embodiment of the present invention, an inspection apparatus is capable of inspecting gratings (wafer features) with pitch ranging e.g., from 0.6 μm to 4 μm. This range covers most of the design rules currently in use in semiconductor manufacturing. The diffraction angles corresponding to two incidence angles as a function of grating pitch (up to 2 μm) are shown in FIGS. 3A and 3B. FIG. 3A shows the relevant incident and diffracted light beams and angles for grating 10. FIG. 3B is a corresponding plot of diffraction angle vs. pitch. These angles are calculated assuming the light wavelength λ to be 546 nm. For higher grating pitches longer wavelengths are used. (This is discussed below.) Each grating type (i.e., gratings with different pitch) will diffract along a unique direction. Consequently, the detector device for detecting one diffracted light is repositioned each time a new grating type is inspected.

Figures 4A, 4B:
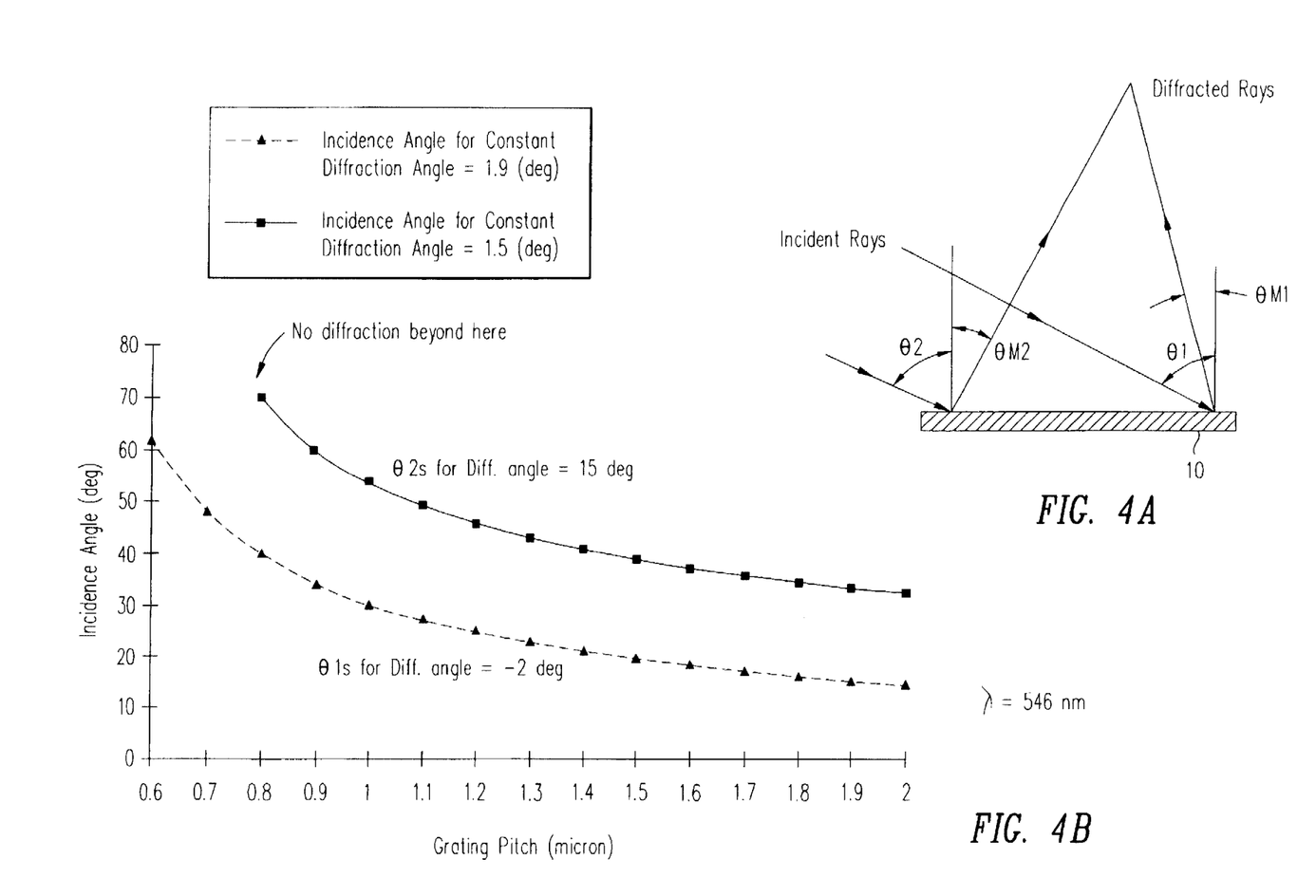
FIG. 4A depicts incident and diffracted light and the relevant angles for two diffraction angles.
FIG. 4B is a plot showing the incidence angle required for different grating pitches when constant diffraction angle is desired, as in FIG. 4A.

In another embodiment, the detector device position is fixed so that the diffraction angle is the same for all grating types. This requires that the light incidence angle be different for each grating type. An example of this is shown in FIGS. 4A and 4B. In FIG. 4B, change in incidence angles θ1 and θ2 is plotted as a function of grating pitch for fixed diffraction angles θM11 (=−2°) and θM21 (=15°). θM11 is the first order diffraction angle corresponding to incidence angle θ1, and θM21 is the first order diffraction angle corresponding to incidence angle θ2 depicted in FIG. 4A. At these diffraction angles, the detector device (not shown) is positioned approximately directly over the grating 10. To implement this, the range of incidence angles required across, e.g. an eight inch diameter semiconductor wafer (the grating 10) is from 14° to 70°. The site of the light source (not shown) to provide the required spread in incidence angles is about 24"×24". Wafers with a certain grating pitch may not be amenable to complete inspection. For example, grating features with pitch 0.6 μm and 0.7 μm cannot be inspected since light incident on those features will not satisfy the diffraction condition, as shown in FIG. 4B.

Figure 5:
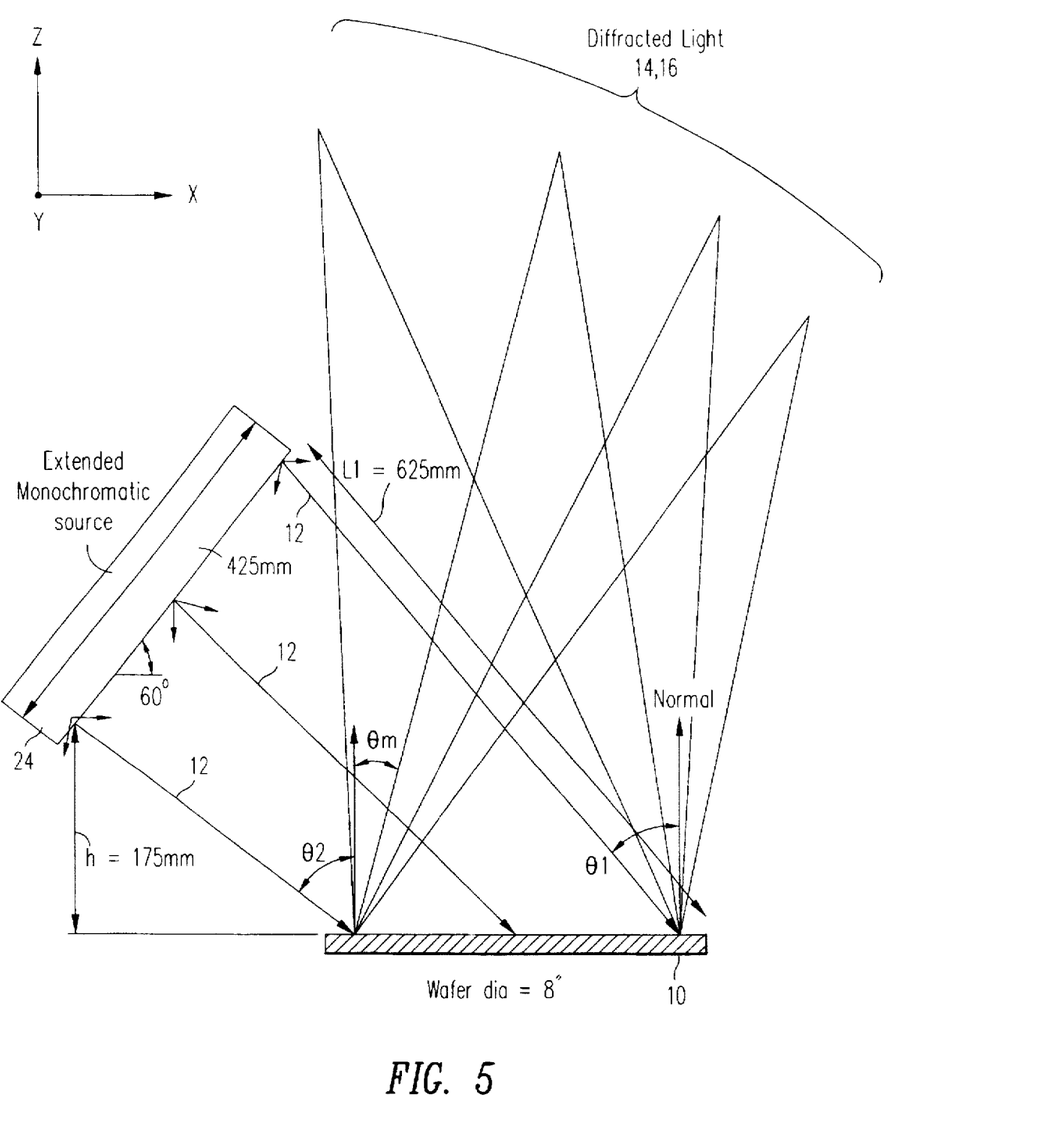
FIG. 5 shows diagrammatically a location of a light source and orientations of the diffracted beams with respect to the plane of a grating.
Figure 6:
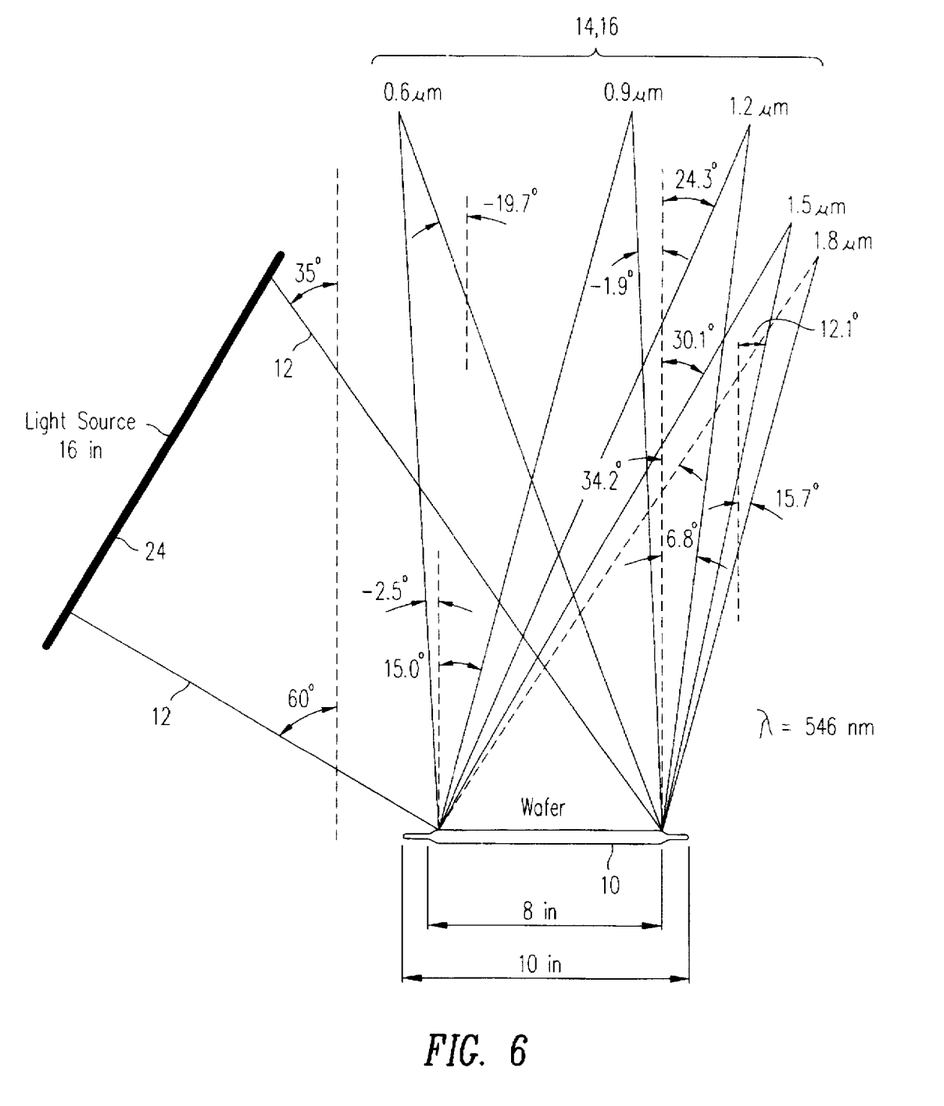
FIG. 6 shows diffraction from a grating, e.g. the surface of a semiconductor wafer, having different feature pitches.

An exemplary inspection apparatus in accordance with this invention is shown schematically in FIG. 5 where the distance L1 from grating 10 to light source 24 is 625 mm and the dimension h is 175 mm. A 60° tilt with respect to the x-axis is assumed for the light source 24. With this arrangement, the angle of incidence of incident light 12 varies from 35°(=θ1) to 60°(=θ2) across e.g. an eight inch diameter wafer 10. In one embodiment, these angles are the same for all grating types. The orientation of the first order diffracted light beams with respect to the wafer normal for five different grating types is shown in FIG. 6 for an 8" diameter wafer 10. (Only first order diffraction is shown here.)

Figure 7:
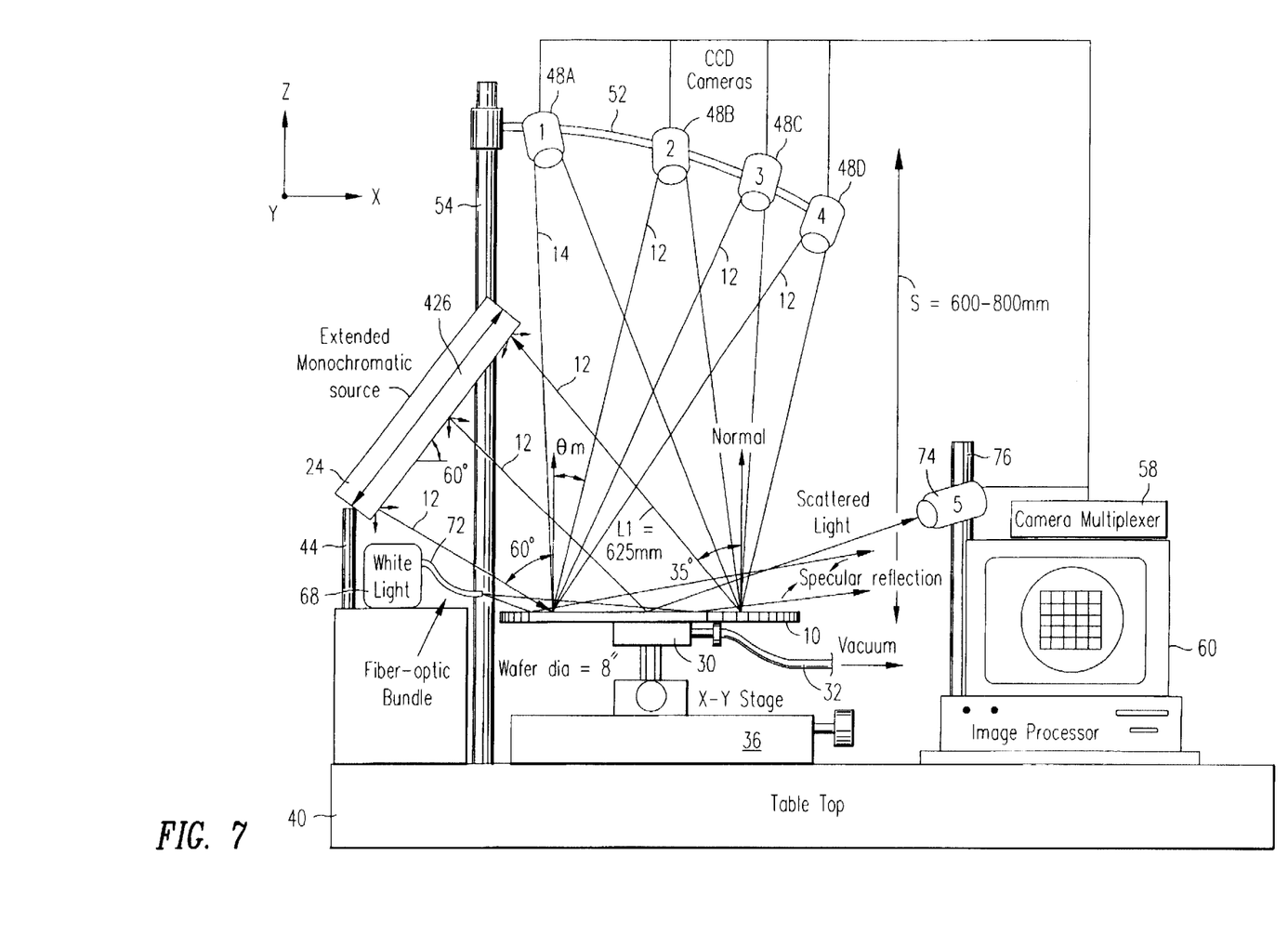
FIG. 7 shows diagrammatically a semiconductor wafer inspection station having multiple detectors.

Further, in one embodiment of this apparatus as shown in more detail in FIG. 7, several cameras (detectors) are used. The multiple CCD (charge coupled device) video cameras 48A, 48B, 48C, 48D in this embodiment are positioned such that each camera receives the designated first order beam 12 from one grating type. The use of CCD cameras as the detectors is illustrative, not limiting. FIG. 7 also shows wafer vacuum chuck 30 on which wafer 10 is held by vacuum supplied through tubing 32, and X-Y stage 36 for translating chuck 30 in the X-Y plane. Stage 36 rests on support ("tabletop") 40. Light source 24 also is supported on table top 40 by support member 44. Multiple CCD cameras 48A, 48B, 48C, 48D (the detectors) are mounted on a guide beam 52 which in turn is held by vertical support 54. The number of cameras needed for semiconductor industry standard Class 2 defect inspection depends on the number of grating types that are to be inspected.

Cameras 48A, . . . , 48D provide their output signals (via camera multiplexer 58) to a commercially available type image processor unit 60. Through camera multiplexing, automatic inspection of different grating types is achieved with a single image processor unit 60. The position of each camera 48A, . . . , 48D in the vertical plane varies in this example from 500 mm to 600 mm from the plane of wafer 10. (For clarity, only four of the five cameras used in one embodiment are shown in FIG. 7. The X-Y-Z axes are shown for orientation purposes.)

In this apparatus, one can pre-position the cameras 48A, . . . , 48D to receive diffracted light if the grating types are known prior to inspection. This reduces the overall inspection time and minimizes operator involvement during inspection set-up. Another advantage is that absence of wafer tilt eliminates errors associated with the wafer tilt due to inaccuracy and repeatability. (This is the tilt of the wafer about the Y axis). Wafer tilt is required if only one camera is used and its position is fixed. By tilting the wafer, one can change the angle of incidence until the diffracted light reaches the camera, as shown in FIG. 4A.

In another embodiment, a single detector (camera) 48A is moved along the guide beam 52 as and when required. This makes the apparatus simple and less complex in terms of setup. However, aligning the single CCD camera to diffracted light each time a wafer with different grating pitch is examined may prolong inspection time and increase operator involvement during set-up.

Figure 8:
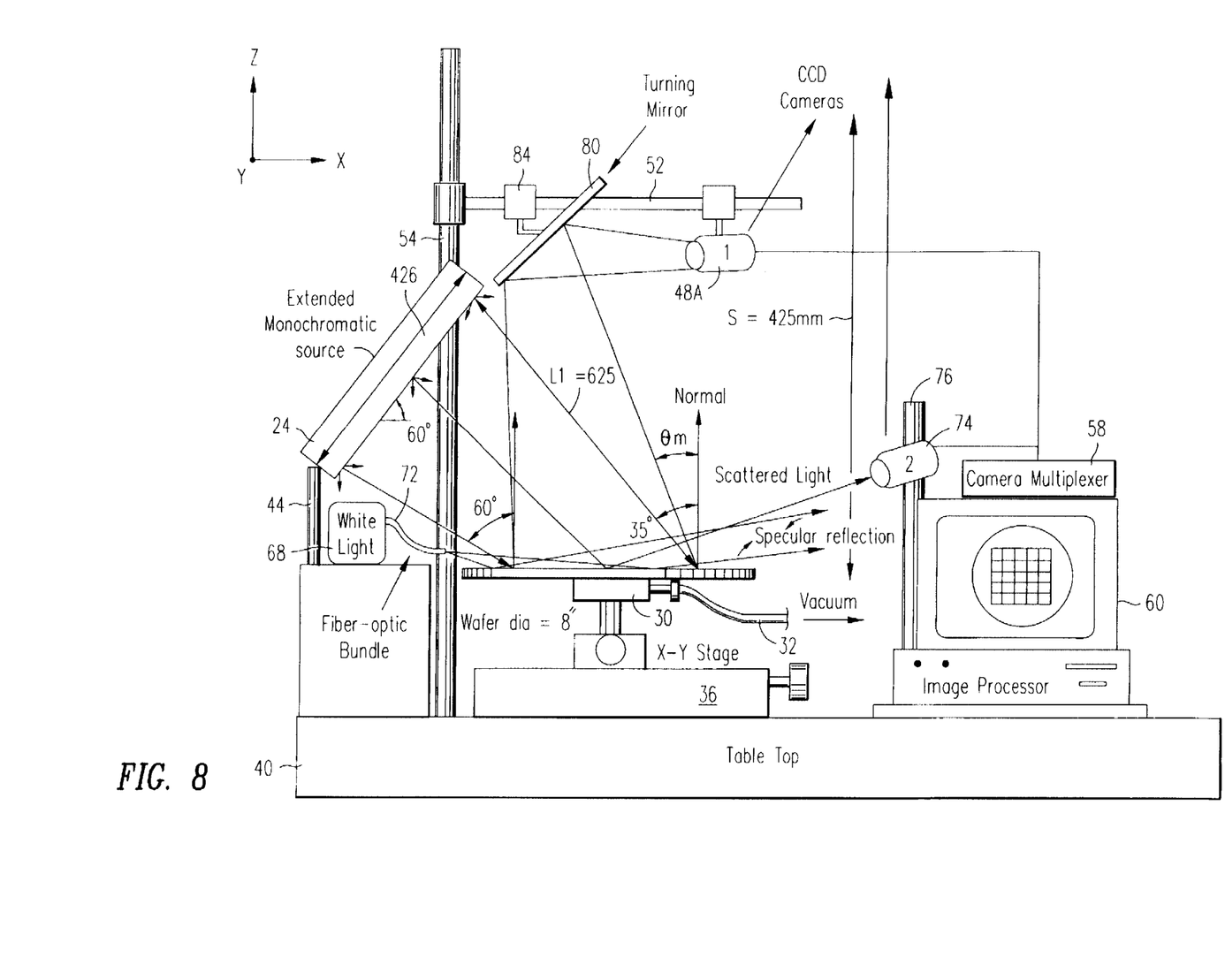
FIG. 8 shows an apparatus similar to that of FIG. 7 but having a single detector camera and a turning mirror for reflecting the diffracted light to the single detector camera.

FIG. 8 shows another embodiment of the present apparatus including the elements of that of FIG. 7 but only having one camera 48A and also having a turning (tilting) mirror 80 that deflects the diffracted light to one side mechanically. By tilting the turning mirror 80 by tilting mechanism 84 and by orienting the detector camera 48A appropriately, light from different grating types is detected and processed.

Only one turning (tilting) mirror 80 as in FIG. 8 is used if the diffracted light is deflected along the X-axis, since the presence of other mirrors may obstruct light from other grating types from reaching the associated camera. However, if the light is directed along the Y-axis, then more than one mirror and one camera can be included. It is possible to include as many cameras as are required. The cameras can be pre-positioned if the grating pitches and feature sizes are known prior to inspection.

An advantage of the FIG. 8 apparatus over that of FIG. 7 is that the FIG. 8 apparatus is more compact in the vertical direction.

Also shown in FIGS. 7 and 8 is a white light source 68 outputting intense white light via fiber optic bundle 72 to be scattered by the surface of wafer 10 to be received by CCD detector camera 74 on support 76. This arrangement is for particle detection. The fiber-optic bundle 72 is positioned so that its light is incident at a grazing angle to the wafer 10 surface. CCD camera 74 is positioned at appropriate meridional and azimuthal angles to sense forward scattered light and is coupled to camera multiplexer 58. By optimizing the three angles, signal to background and signal to noise ratios of the camera 74 are optimized. This particle detection is not necessary to the present apparatus or the present invention.

Figure 9:
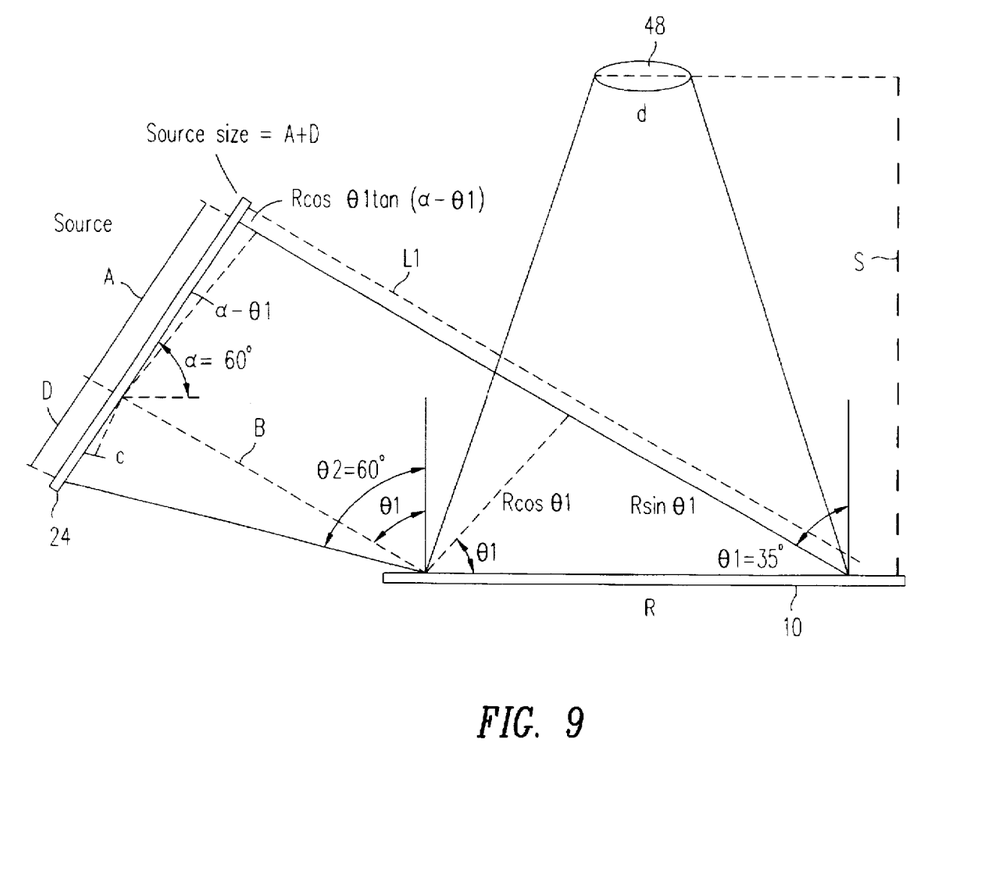
FIG. 9 shows diagrammatically how to determine the length of the light source as a function of the diameter of the grating to be inspected.

The light source size for each of the above embodiments, in terms of length and width, is determined as shown in FIG. 9. Let L1 be the distance between the grating 10 and the light source 24 as shown in the above figure. $\alpha$ is the tilt of the light source 24 with respect to the x-axis. The size of the light source 24 required to view a wafer 10 of diameter R under diffracted light is then given by:

$$source\ size = R\cos\theta 1/\cos(\alpha - \theta 1) + (L1 - R\sin\theta 1 - R\cos\theta 1 \tan(\alpha - \theta 1))\sin(\theta 2 - \theta 1)/\cos y$$

For an 8" diameter wafer (grating) with $\theta 1=35°$ and $\theta 2=60°$, the size (length) of the source in the direction shown is 16". The source dimension in the orthogonal direction (width) is also very close to 16".

A disadvantage of single field inspection of an entire grating by such an elongated extended source is that two adjacent diffraction orders can overlap when the grating pitch 'd' becomes larger. The condition for overlap is as follows:

$$\sin\theta_{i2} = \lambda/d + \sin\theta_{i1} \tag{2}$$

where 1 and 2 refer to diffraction order, and $\theta_i$ refers to the angles of incidence for those orders that produce the same diffraction angle from the same point on the grating. For example, consider diffraction from the right hand edge of an eight inch diameter wafer with 1.8µ grating pitch. A first order diffracted image produced by $\theta_{i1}=35°$ overlaps with the second order image of that edge generated by light incident at $\theta_{i2}=61.27°$. Light rays contributing to $\theta_{i2}$ generally originate from the bottom part of the extended source, hence the overlap is minimal. If the "Golden Image" (i.e., the defect free statistical image used for image analysis to find defect sites) includes these rays, then inspection may not produce false rejection due to this overlap. Also when the grating under inspection has a line width to pitch ratio of 0.5, the second order is suppressed thereby eliminating overlap concerns. In accordance with this invention the overlap problem is avoided by increasing the wavelength $\lambda$ of the source to an appropriate value. In the embodiment shown in FIGS. 7 and 8, the source wavelength is increased from 546 nm to 880 nm.

Another disadvantage of single field inspection is the overlap between mth order diffraction and specularly reflected light (i.e., zero order diffraction). This occurs when:

$$\sin\theta_{is} = m\lambda/d + \sin\theta_{im} \tag{3}$$

where $\theta_{is}$ is the incidence angle of the specularly reflected light, $\theta_{im}$ is the incidence angle that generates mth order diffraction. Light rays contributing to $\theta_{is}$ generally originate from the top part of the extended source. If the Golden Image includes these rays, then inspection does not produce false rejection due to this overlap.

Figure 10:
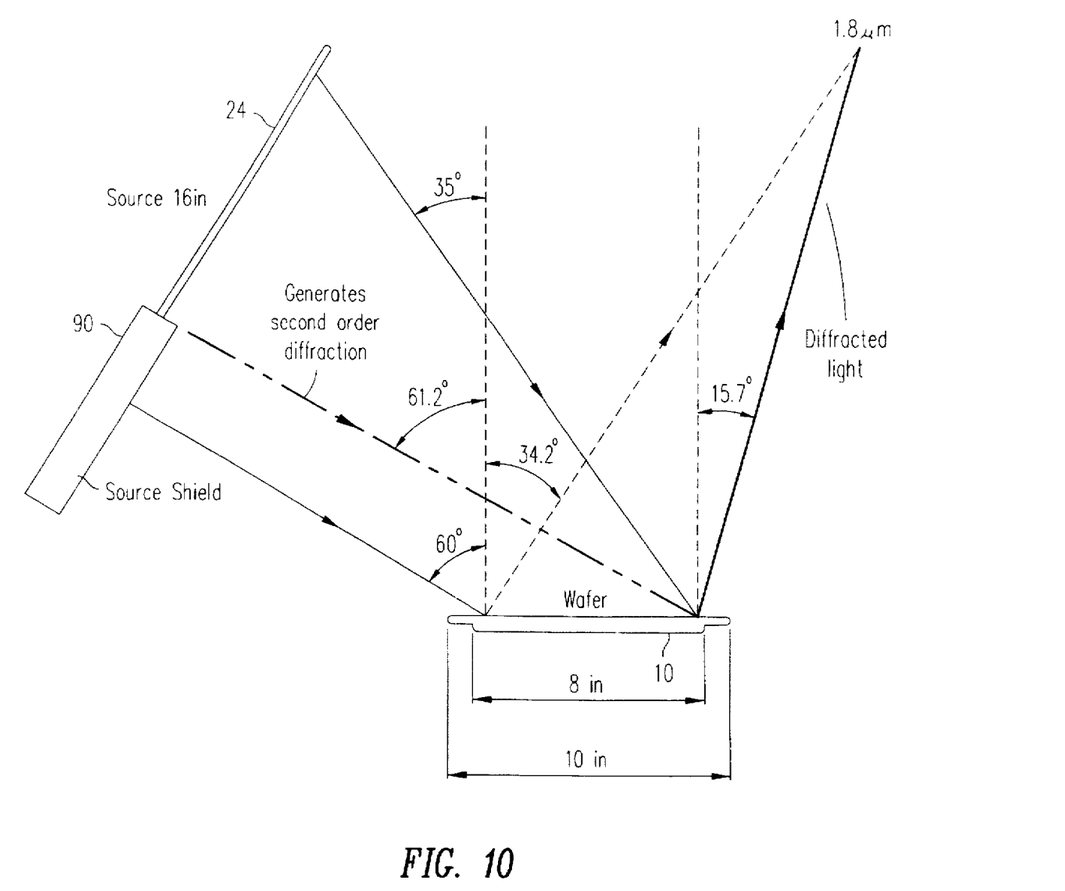
FIG. 10 shows partial shielding of the light source to avoid second order diffraction effects.
Figure 11:
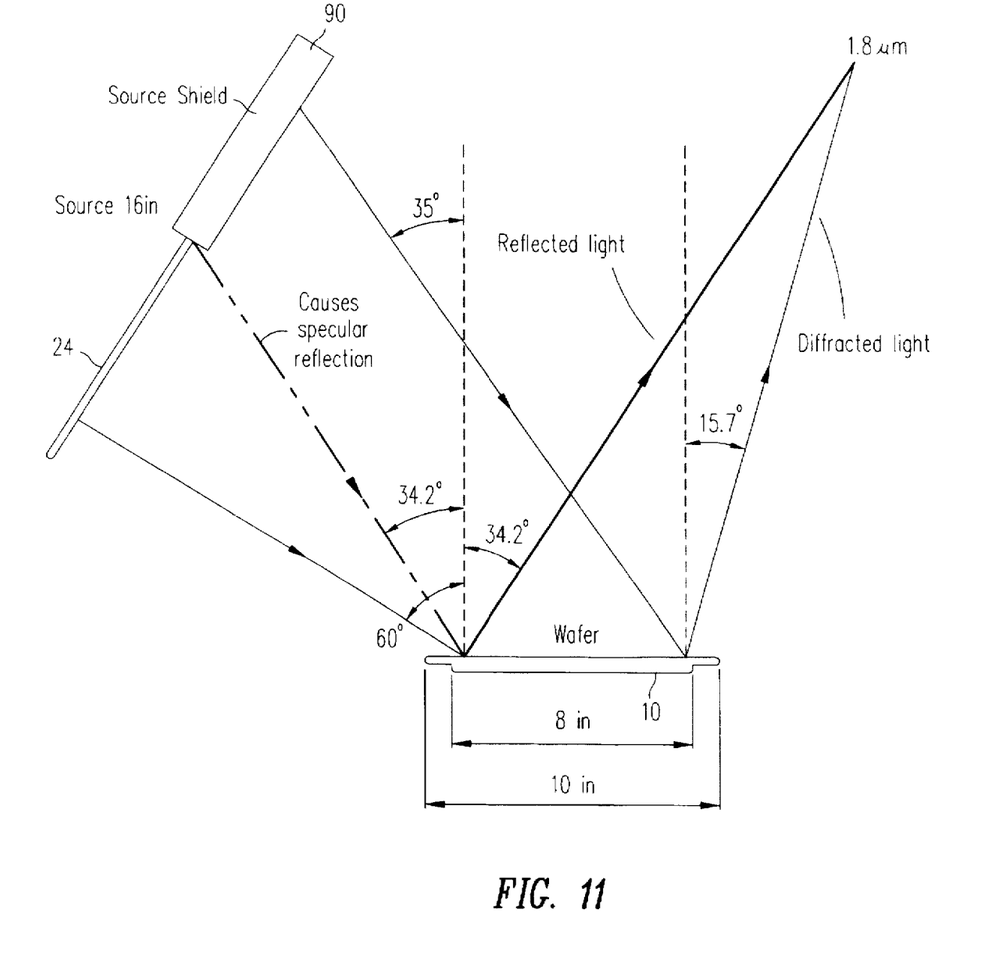
FIG. 11 shows partial shielding of the light source to avoid specular reflection.
Figure 12:
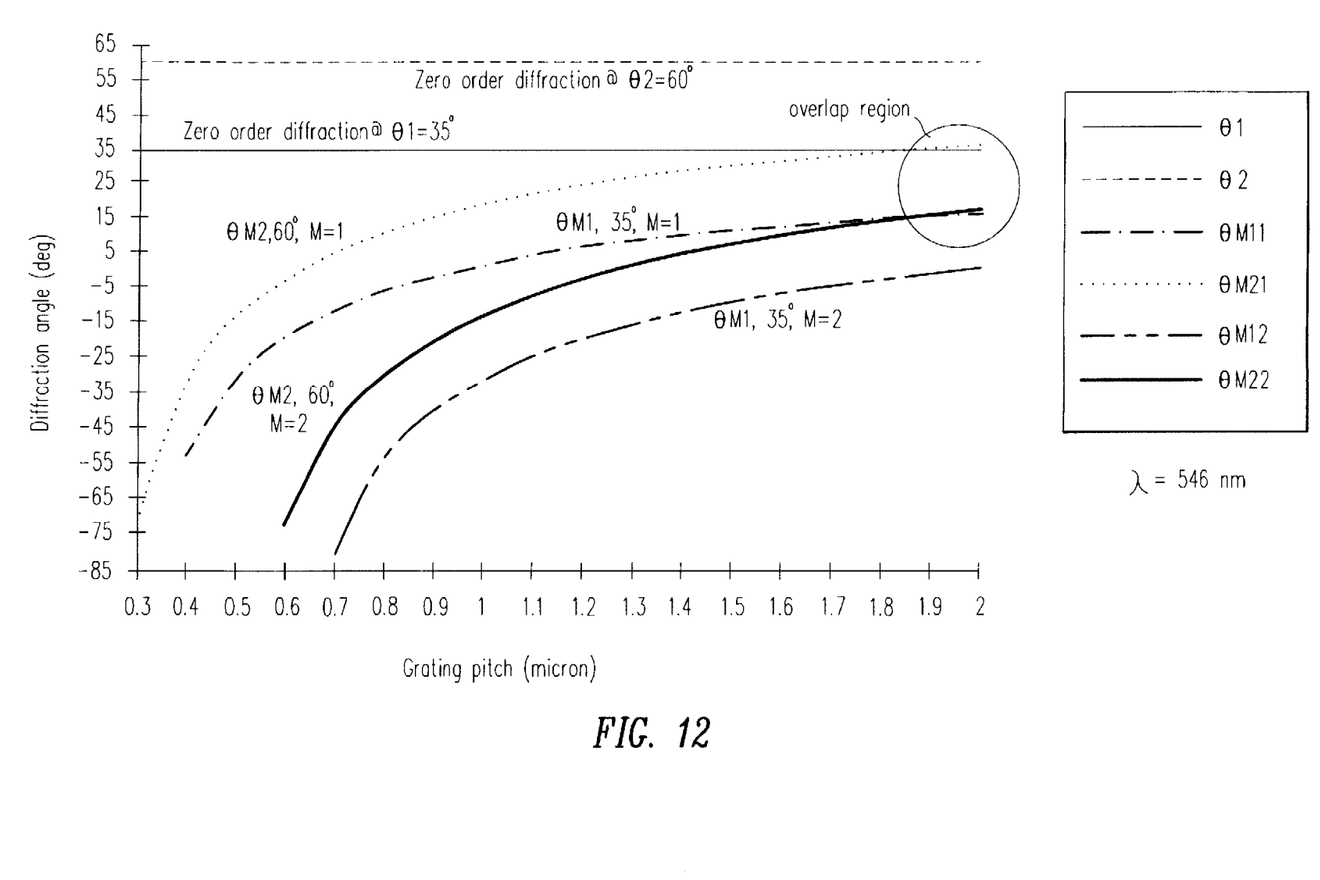
FIG. 12 shows first and second order diffraction order overlap at 1.8 μm pitch and higher for two incident angles when 546 nm light is used.

If overlap is to be avoided, then inspection of a grating with larger pitch is performed in two parts. First, one inspects the right half of the wafer using light only from the top part of the source, i.e. one shields the bottom part of the source as shown in FIG. 10 with shield 90. This prevents overlap between adjacent diffraction orders. Next, one inspects the left half of the wafer using light from the bottom part of the source with its top part shielded as shown in FIG. 11 with shield 90 moved to the other end of source 10. This prevents overlap between diffracted light and specularly reflected light. In FIG. 12 diffraction angles for three diffraction orders (m=0, 1 and 2) as a function of grating pitch are plotted. Cross over points correspond to the overlap between orders.

In some embodiments of this invention, a single wavelength monochromatic light source is used. Sometimes a single apparatus is used to inspect a range of grating types, namely, pitches of 0.6μ to 4μ. As the grating pitch increases, the angular separation $\Delta\theta_m$ between adjacent orders will decrease as:

$$\Delta\theta_m = \sin^{-1}(\Delta m \lambda/d) \quad (4)$$

Moreover, as seen from equation (2) for a given wavelength, $\sin\theta_{i2}$ approaches $\sin\theta_{i1}$ when there is a considerable increase in 'd'. This means that the overlapping orders are produced by incident light coming from close by regions in the source and not from its extremities. When this happens, the problem of order overlap becomes more severe and small intensity variations caused by Class 2 defects may not be detected.

Figure 13:
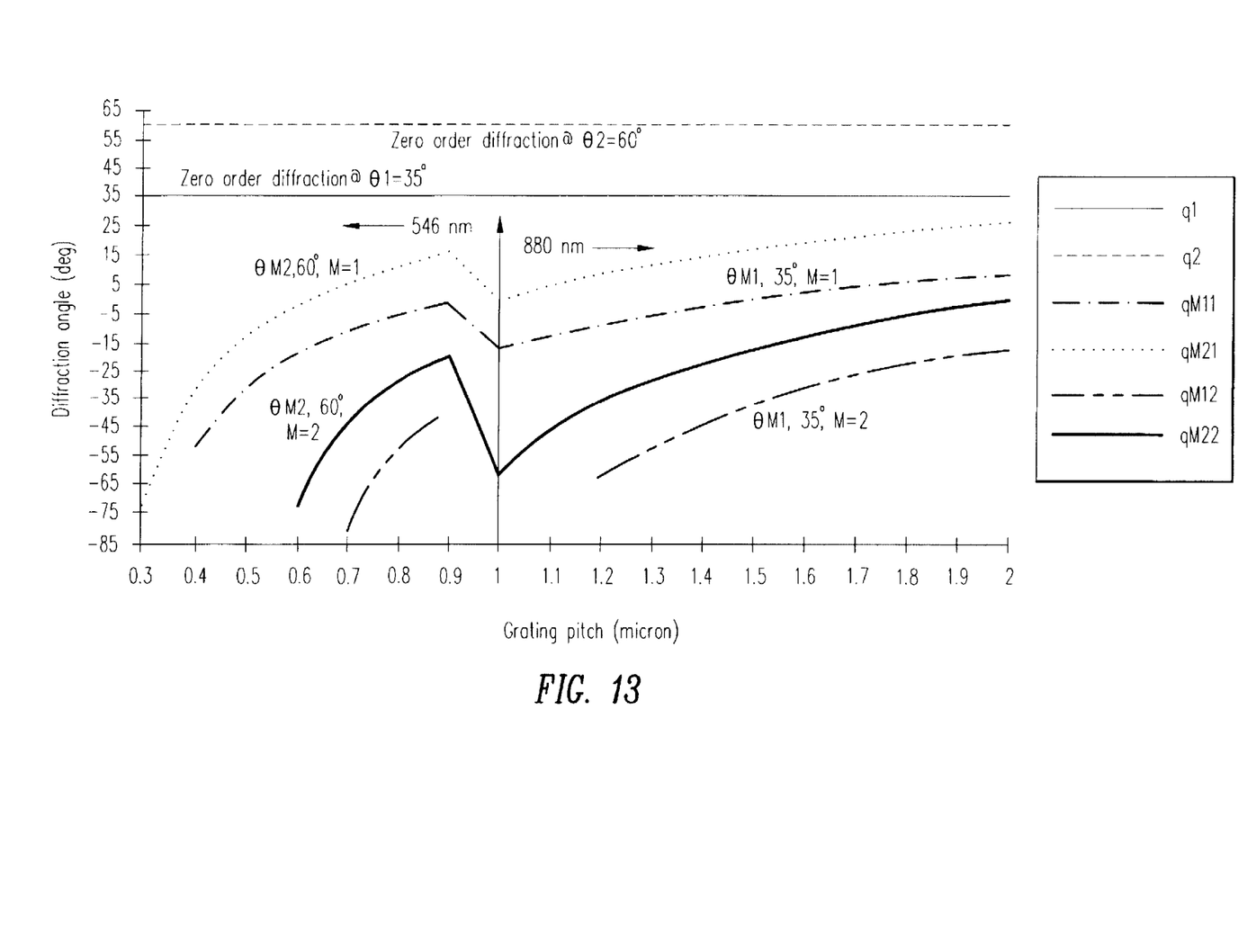
FIG. 13 shows elimination of first and second order diffraction overlap when the wavelength is increased to 880 nm.

The above problem is mitigated to a large extent by using a longer wavelength light source. The plot of FIG. 13 shows that by using 880 nm wavelength light, order overlap encountered in lower periodicity gratings is removed. Moreover, a commercially available silicon CCD camera has fairly good responsivity to this wavelength. Commercially available GaAlAs light emitting diodes emit at 880±40 nm light. An extended source having of a large number of these LEDs in a two dimensional array is the light source in one embodiment.

Figure 14:
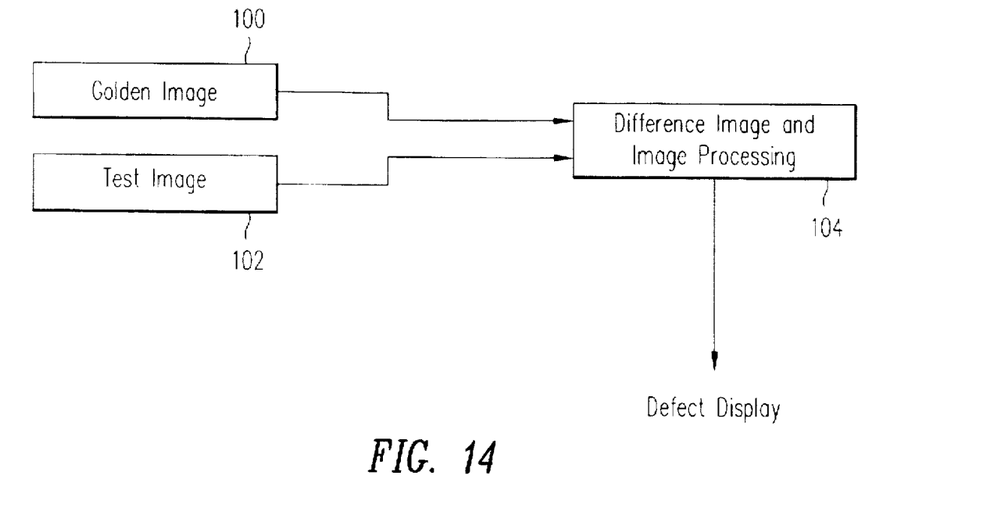
FIG. 14 shows diagrammatically the image processing procedure.

To automate defect detection, the wafer images are acquired using machine vision circuitry, e.g. the Model 3400 from Cognex Corp. and analyzed using "Golden Template Comparison" (GTC) software commercially available from Cognex Corp. running on a general purpose computer. The GTC process is shown diagrammatically in FIG. 14. The Golden Image 100 is the defect free nominal signal, as used for instance in the commercially available GTC software. This Golden Image 100 is compared to the test image 102 (from the wafer under inspection) and subject to difference image and image processing 104 by the software, to provide a defect display.

Typically the data values supplied to the image processing software are intensity threshold values. GTC carries out a pixel to pixel comparison and displays a thresholded difference image. Hence the smallest detectable defect size relates to the pixel size of the CCD cameras in the detector system and system magnification.

In one embodiment, the detector signal is compared to an arbitrarily chosen signal. However, it has been found that it is more effective instead to "train" the software on actual "good" gratings, which are physical gratings which are first inspected by other means to determine that they are defect free, or at least defect free over a given portion of their area. Such training is undertaken e.g. for each semiconductor process step for which it is desired to inspect the actual wafers under inspection. Thus after the software is trained on the good gratings, so it has stored in memory the data pertaining to the good gratings for every semiconductor process step of interest, one proceeds to inspect the actual wafers under inspection by acquiring the wafer images as described above. The image data (the diffracted light intensity on a pixel basis) is then compared to the stored data by the above-described GTC software.

After finding a particular defect (in the wafer) one conventionally sends that wafer to the review station for defect review and if necessary (and possible) reworks the wafer.

This disclosure is illustrative and not limiting. Further modifications to the invention will be apparent to one of ordinary skill in the art in light of this disclosure and are intended to fall within the scope of the appended claims.

We claim:

1. A method of inspecting for defects in features having a periodic structure defined on a surface of a substrate, comprising the steps of:

directing light incident onto the surface of the substrate;
   detecting light diffracted from the surface of the substrate wherein the diffraction is of first order or greater;
   determining an efficiency of diffraction of the diffracted light; and
   determining a presence or absence of a local defect in the features on the substrate from the determined efficiency.

2. A method of inspecting for defects in features having a periodic structure defined on a surface of a substrate, comprising the steps of:

directing light incident onto the surface of the substrate;
   detecting light diffracted from the surface of the substrate;
   determining an efficiency of diffraction of the diffracted light; and
   determining a presence or absence of a local defect in the features on the substrate from the determined efficiency;
   wherein the periodic structure of the features is defined by a particular width and pitch, and wherein the step of directing light comprises directing light of a wavelength that is a function of the particular width and pitch.

3. The method of claim 1, wherein the incident light is monochromatic.

4. A method of inspecting for defects in features having a periodic structure defined on a surface of a substrate, comprising the steps of:

directing light incident onto the surface of the substrate;
   detecting light diffracted from the surface of the substrate;
   determining an efficiency of diffraction of the diffracted light; and
   determining a presence or absence of a local defect in the features on the substrate from the determined efficiency;
   wherein the features on the surface of the substrate are of a plurality of widths and pitches, and wherein the step of directing light comprises the step of directing light of a plurality of wavelengths onto the surface of the substrate.

5. The method of claim 1, wherein the step of directing light comprises the step of providing the light from an elongated and extended source of light.

6. A method of inspecting for defects in features having a periodic structure defined on a surface of a substrate, comprising the steps of:

directing light incident onto the surface of the substrate;
detecting light diffracted from the surface of the substrate;
determining an efficiency of diffraction of the diffracted light; and
determining a presence or absence of a local defect in the features on the substrate from the determined efficiency; wherein the step of determining comprises the steps of:
providing another substrate having features defined in its surface having a pitch and width similar to that of the substrate to be inspected, and known to be free of defects; and
determining an efficiency of diffraction of the surface of the another substrate, thereby arriving at a known efficiency of diffraction; and
comparing the known efficiency of diffraction to the efficiency of diffraction of the substrate.

7. A method of inspecting for defects in features having a periodic structure defined on a surface of a substrate, comprising the steps of:

directing light incident onto the surface of the substrate;
detecting light diffracted from the surface of the substrate;
determining an efficiency of diffraction of the diffracted light; and
determining a presence or absence of a local defect in the features on the substrate from the determined efficiency:
wherein the step of detecting comprises detecting the diffracted light at a plurality of angles relative to a path of the incident light;
where the step of detecting at a plurality of angles comprises providing a plurality of detectors, one located at each of the plurality of angles.

8. The method of claim 7, wherein the step of detecting at a plurality of angles comprises moving a single detector to each of the plurality of angles.

9. A method of inspecting for defects in features having a periodic structure defined on a surface of a substrate, comprising the steps of:

directing light incident onto the surface of the substrate;
detecting light diffracted from the surface of the substrate;
determining an efficiency of diffraction of the diffracted light; and
determining a presence or absence of a local defect in the features on the substrate from the determined efficiency;
wherein the features on the surface of the substrate are of a plurality of widths and pitches, and wherein the step of detecting comprises the step of detecting the diffracted light at a plurality of angles relative to a path of the incident light, each angle corresponding to a particular feature pitch and width.

10. The method of claim 1, wherein the steps of detecting comprises detecting by a charge coupled device camera.

11. The method of claim 1, wherein the defects are in one of a group of material layers on the substrate, the group consisting of layers of silicon, metal, polysilicon, photoresist, silicon oxide, and other materials used in semiconductor manufacturing.

12. The method of claim 1, wherein the step of directing light comprises the step of directing light from all points of the source to all points on the surface of the substrate.

13. The method of claim 1, wherein the step of detecting comprises detecting light diffracted from all of the surface of the substrate.

14. A method of inspecting for defects in features having a periodic structure defined on a surface of a substrate, comprising the steps of:

directing light incident onto the surface of the substrate;
detecting light diffracted from the surface of the substrate;
determining an efficiency of diffraction of the diffracted light;
determining a presence or absence of a local defect in the features on the substrate from the determined efficiency;
rotating the substrate in a plane defined by its surface; and
detecting light diffracted from the surface of the substrate before and after the step of rotating, thereby determining an efficiency of diffraction of the surface at a plurality of orientations of the substrate.

15. The method of claim 1, further comprising the step of diffusing the incident light.

16. The method of claim 1, wherein the substrate is one of a group consisting of a semiconductor wafer, a micromachined structure, and a diffraction grating.

17. A method of inspecting for defects in features having a periodic structure defined on a surface of a substrate, comprising the steps of:

directing light incident onto the surface of the substrate;
detecting light diffracted from the surface of the substrate;
determining an efficiency of diffraction of the diffracted light;
determining a presence or absence of a local defect in the features on the substrate from the determined efficiency;
wherein the step of directing light comprises the step of providing the light from an elongated and extended source of light;
providing light from only a first portion of the source onto only a first portion of the surface of the substrate; and
providing the light from only a second portion of the source onto only a second portion of the surface of the substrate.

18. The method of claim 1, wherein the efficiency of diffraction is a ratio of an intensity of the incident light to an intensity of the detected diffracted light.

19. The method of claim 1, further comprising the step of directing polychromatic light onto the surface of the substrate, thereby to detect particles present on the surface of the wafer.

20. An apparatus to inspect for defects in a substrate having features defining a periodic structure on its surface, comprising:

a support to hold the substrate;
a source of light located to direct light onto the surface of the substrate when the substrate is on the support;
a detector located to receive light diffracted from the surface of the substrate, wherein the diffraction is of first order or greater; and
a processor coupled to the detector to determine an efficiency of diffraction of the received light, thereby to determine a presence or absence of a local defect in the features on the surface of the substrate.

21. The apparatus of claim 20, wherein the source of light provides monochromatic light.

22. The apparatus of claim 20, wherein the source of light provides light of a plurality of wavelengths.

23. The apparatus of claim 20, wherein the source of light is extended and elongated.

24. The apparatus of claim 23, wherein the source of light is at least 30 cm. long.

25. An apparatus to inspect for defects in a substrate having features defining a periodic structure on its surface, comprising:

a support to hold the substrate;

a source of light located to direct light onto the surface of the substrate when the substrate is on the support;

a first detector located to receive light diffracted from the surface of the substrate;

a processor coupled to the detector to detect an efficiency of diffraction of the received light, thereby to determine a presence or absence of a local defect in the features on the surface of the substrate; and at least one additional detector located to receive light diffracted from the surface of the substrate, the additional detector being located to detect light diffracted at a different angle than is the first detector.

26. The apparatus of claim 20, further comprising a mechanism coupled to the detector to move the detector relative to the support.

27. The apparatus of claim 20, wherein the detector detects light diffracted from the substrate at a plurality of angles.

28. The apparatus of claim 20, wherein the detector comprises a charged coupled device camera.

29. The apparatus of claim 20, wherein the support includes an XY stage.

30. The apparatus of claim 20, wherein the support includes a mechanism to rotate the substrate in a plane defined by its surface.

31. An apparatus to inspect for defects in a substrate having features defining a periodic structure on its surface, comprising:

a support to hold the substrate;

a source of light located to direct light onto the surface of the substrate when the substrate is on the support;

a detector located to receive light diffracted from the surface of the substrate;

a processor coupled to the detector to detect an efficiency of diffraction of the received light, thereby to determine a presence or absence of a local defect in the features on the surface of the substrate; and a diffuser interposed between the source of light and the support.

32. An apparatus to inspect for defects in a substrate having features defining a periodic structure on its surface, comprising:

a support to hold the substrate;

a source of light located to direct light onto the surface of the substrate when the substrate is on the support;

a detector located to receive light diffracted from the surface of the substrate;

a processor coupled to the detector to detect an efficiency of diffraction of the received light, thereby to determine a presence or absence of a local defect in the features on the surface of the substrate; and a mechanism to direct light from only a first portion of the source of light onto only a first portion of the substrate, and from only a second portion of the source of light onto only a second portion of the substrate.

33. An apparatus to inspect for defects in a substrate having features defining a periodic structure on its surface, comprising:

a support to hold the substrate;

a source of light located to direct light onto the surface of the substrate when the substrate is on the support;

a detector located to receive light diffracted from the surface of the substrate;

a processor coupled to the detector to detect an efficiency of diffraction of the received light, thereby to determine a presence or absence of a local defect in the features on the surface of the substrate;

a second light source located to direct polychromatic light onto the surface of the substrate; and a director located to receive polychromatic light scattered from the surface of the substrate.

34. An apparatus to inspect for defects in a substrate having features defining a periodic structure on its surface, comprising:

a support to hold the substrate;

a source of light located to direct light onto the surface of the substrate when the substrate is on the support;

a detector located to receive light diffracted from the surface of the substrate;

a processor coupled to the detector to detect an efficiency of diffraction of the received light, thereby to determine a presence or absence of a local defect in the features on the surface of the substrate; and a mechanism coupled to the detector for moving the detector relative to the support;

wherein the mechanism comprises:

a camera stationary respected to the support; and a movable reflective element located to receive the light diffracted from the surface of the substrate, and to direct the received light onto the camera.

35. The apparatus of claim 25, further comprising a multiplexer coupled between the processor and each of the detectors.

36. The apparatus of claim 20, wherein the light source directs light from a plurality of spaced apart points on the light source onto all parts of the surface of the substrate.

37. An apparatus to inspect for defects in a three dimensional periodic structure defined on a surface of a substrate, the apparatus comprising:

means for supporting the substrate;

means for directing light incident onto the substrate;

means for detecting light diffracted from the periodic structure, wherein the diffraction is of first order or greater; and means for determining an intensity of the detected light, thereby to determine a defect in the periodic structure.

38. The apparatus of claim 24, wherein the source of light is at least 30 cm wide.

39. The method of claim 1, where the step of determining comprises comparing an efficiency of diffraction of the diffracted light to a known efficiency of diffraction.

40. The apparatus of claim 20, wherein the processor determines the efficiency by comparing the efficiency of the received light to a known efficiency of diffraction.

* * * * *